US012807915B2

(12) United States Patent
Zhang et al.

(10) Patent No.: US 12,807,915 B2
(45) Date of Patent: Nov. 24, 2026

(54) SPLIT SHAKER AND INCUBATOR COMPRISING THE SAME

(71) Applicant: Shinetek Instrument Research Institute, Beijing (CN)

(72) Inventors: Cheng Xiang Zhang, Beijing (CN); Heng Su, Beijing (CN)

(73) Assignee: Shinetek Instrument Research Institute, Beijing (CN)

( * ) Notice: Subject to any disclaimer, the term of this patent is extended or adjusted under 35 U.S.C. 154(b) by 1275 days.

(21) Appl. No.: 17/524,229

(22) Filed: Nov. 11, 2021

(65) Prior Publication Data

US 2022/0145229 A1 May 12, 2022

(30) Foreign Application Priority Data

Nov. 12, 2020 (CN) ........................ 202011262106.0

(51) Int. Cl.

| | |
|---|---|
| ***B01F 31/20*** | (2022.01) |
| ***B01F 31/22*** | (2022.01) |
| ***B01F 101/23*** | (2022.01) |
| ***C12M 1/00*** | (2006.01) |
| ***C12M 3/00*** | (2006.01) |
| ***C12M 3/06*** | (2006.01) |

(52) U.S. Cl.
CPC ............. *C12M 27/16* (2013.01); *B01F 31/22* (2022.01); *B01F 31/27* (2022.01); *C12M 41/14* (2013.01); *B01F 31/201* (2022.01); *B01F 2101/23* (2022.01); *C12M 23/48* (2013.01)

(58) Field of Classification Search
CPC ...... C12M 27/16; C12M 41/14; C12M 23/48; C12M 23/02; C12M 23/34; C12M 41/00; C12M 41/42; B01F 31/22; B01F 31/27; B01F 31/201; B01F 2101/23; B01F 31/24; B01F 31/265
See application file for complete search history.

(56) References Cited

U.S. PATENT DOCUMENTS 3,911,836 A * 10/1975 Brown .................... F23J 15/04 110/215
5,409,312 A 4/1995 Fletcher
(Continued)

FOREIGN PATENT DOCUMENTS

CN 201598279 U 10/2010
CN 105624644 A * 6/2016
(Continued)

OTHER PUBLICATIONS

Office Action of corresponding DE application (DE10 2021 128 620.4) Oct. 24, 2023.
(Continued)

*Primary Examiner* — Liban M Hassan
(74) *Attorney, Agent, or Firm* — Rankin, Hill & Clark LLP

(57) ABSTRACT

A split shaker for an incubator, the incubator defining an incubation chamber, wherein the split shaker includes a disk drive motor for driving a shaking table, a disk drive motor including a stator assembly disposed outside the incubation chamber, and a rotor assembly disposed inside the incubation chamber having a central shaft and a rotor turntable mounted on the central shaft; wherein the rotation of the rotor turntable drives a shaking movement of the shaking table.

7 Claims, 2 Drawing Sheets

(56) References Cited

U.S. PATENT DOCUMENTS

| | | | | |
|---|---|---|---|---|
| 2010/0330663 | A1 | 12/2010 | Baumfalk et al. | |
| 2012/0294107 | A1 | 11/2012 | Zamirowski et al. | |
| 2018/0008943 | A1 * | 1/2018 | Corves | F16F 15/363 |
| 2019/0224692 | A1 * | 7/2019 | Beukert | B04B 13/00 |

FOREIGN PATENT DOCUMENTS

| | | | | | |
|---|---|---|---|---|---|
| CN | 105743234 | A | | 7/2016 | |
| CN | 110417157 | A | | 11/2019 | |
| CN | 112410213 | A | | 2/2021 | |
| CN | 112410214 | A | | 2/2021 | |
| CN | 114768631 | A | | 7/2022 | |
| CN | 216864199 | U | | 7/2022 | |
| DE | 102008010780 | B3 | | 10/2009 | |
| DE | 202020105719 | U1 | | 11/2020 | |
| FR | 2134780 | A5 | | 12/1972 | |
| JP | H09154565 | A | * | 6/1997 | C12M 27/16 |
| KR | 20030013354 | A | | 2/2003 | |
| KR | 20130081516 | A | * | 7/2013 | C12M 27/16 |
| KR | 20160089740 | A | * | 7/2016 | C12M 3/00 |
| WO | WO-2004047993 | A1 | * | 6/2004 | B04B 15/02 |
| WO | 2009106248 | A2 | | 9/2009 | |

OTHER PUBLICATIONS

Espacenet Bibliographic data:CN 110417157 (A), Published Nov. 5, 2019, 2 pgs.

* cited by examiner

SPLIT SHAKER AND INCUBATOR COMPRISING THE SAME

PRIORITY

This application claims priority to Chinese Patent Application CN 202011262106.0 filed on Nov. 12, 2020, which is incorporated by reference herein.

FIELD

The present disclosure relates to a shaker, in particular to a split shaker and an incubator comprising the same.

BACKGROUND

For incubators used for microorganism or cell cultivation, the incubation chambers thereof all need to be effectively cleaned and disinfected. For example, this is essential for a Good-Manufacturing-Practice (GMP) compliant cell cultivation. Moreover, a precisely controlled climate in the incubation chamber, such as temperature, humidity, carbon dioxide content, oxygen content, and the like, is necessary to maintain optimal cell culture conditions. Secondly, the space in the incubator is very precious. The design of the shaker should save the space inside the incubator as much as possible to enable placement of more cultures or larger containers into the incubator.

For conventional incubators, the shaker is generally mounted inside the incubator. Some of the shakers comprise belts and other transmission devices to realize the control of a motor to the central output shaft. This structure introduces consumables for transmission such as belts, which are susceptible to the quality of consumables such as belts, resulting in high failure rates and maintenance difficulty. In addition, the internal structure thereof is complex, and the motor is usually arranged on a side surface of the shaker, so that a large space, in particular a large height is occupied, which reduces an overall utilization rate of such device with the same volume. Meanwhile, the shaker including the motor is integrally placed inside the incubator, so that the maintenance of a clean environment in the incubator is greatly influenced due to heating of the motor and contamination of the complex motor structure. For this, in some designs of the incubator, the various components of the shaker are arranged inside and outside the incubation chamber of the incubator respectively.

For example, US 2010/0330663 A1 relates to an incubator with a shaking device. The incubator includes an incubation chamber and a device chamber. The drive arm, drive shaft, eccentric rotary joint and shaking table of the shaker are located in the culture chamber; while the motor and the drive belt are located in the device chamber. The motor drives the drive shaft to rotate via the drive belt. A base plate of the incubator seals the incubation chamber from the device chamber. Some components of the shaker are arranged in the incubation chamber, and the other components are located in the device chamber. The distance between the motor and the shaking table is relatively large, which might cause strong vibration of the shaking table. And due to the complex structure, it is difficult to clean the incubation chamber. In addition, the drive belt and the seals between the two chambers are consumables and need to be replaced regularly.

The present inventors have recognized that the above-described incubator is not easy to clean and occupies an inner space of the incubation chamber.

SUMMARY OF THE INVENTION

The present disclosure provides a split shaker and a corresponding split incubator, to overcome, at least in part, the above defects.

According to an aspect of the present disclosure, a split shaker for an incubator is provided, wherein the incubator defines an incubation chamber. The split shaker includes a disk drive motor for driving the shaking table, the disk drive motor including a stator assembly disposed outside the incubation chamber and a rotor assembly disposed inside the incubation chamber having a central shaft and a rotor turntable mounted on the central shaft; wherein the rotation of the rotor turntable drives a shaking movement of the shaking table.

These and other objects, aspects, features and advantages of the invention will become apparent to those skilled in the art upon a reading of the Detailed Description of the invention set forth below taken together with the drawings which will be described in the next section

BRIEF DESCRIPTION OF THE DRAWINGS

The invention may take physical form in certain parts and arrangement of parts, a preferred embodiment of which will be described in detail and illustrated in the accompanying drawings which forms a part hereof and wherein.

DETAILED DESCRIPTION OF THE INVENTION

Generally, all terms used herein are to be interpreted according to their ordinary meaning in the relevant technical field, unless a different meaning is clearly given and/or is implied from the context in which it is used. All references to a/an/the element, apparatus, component, means, step, etc. are to be interpreted openly as referring to at least one instance of the element, apparatus, component, means, step, etc., unless explicitly stated otherwise. Any feature of any of the embodiments disclosed herein may be applied to any other embodiment, wherever appropriate. Likewise, any advantage of any of the embodiments may apply to any other embodiments, and vice versa. Other objectives, features, and advantages of the enclosed embodiments will be apparent from the following description.

Some of the embodiments contemplated herein will now be described more fully with reference to the accompanying drawings. Other embodiments, however, are contained within the scope of the subject matter disclosed herein, the disclosed subject matter should not be construed as limited to only the embodiments set forth herein. Rather, these embodiments are provided by way of example to convey the scope of the subject matter to those skilled in the art.

Figure 1:
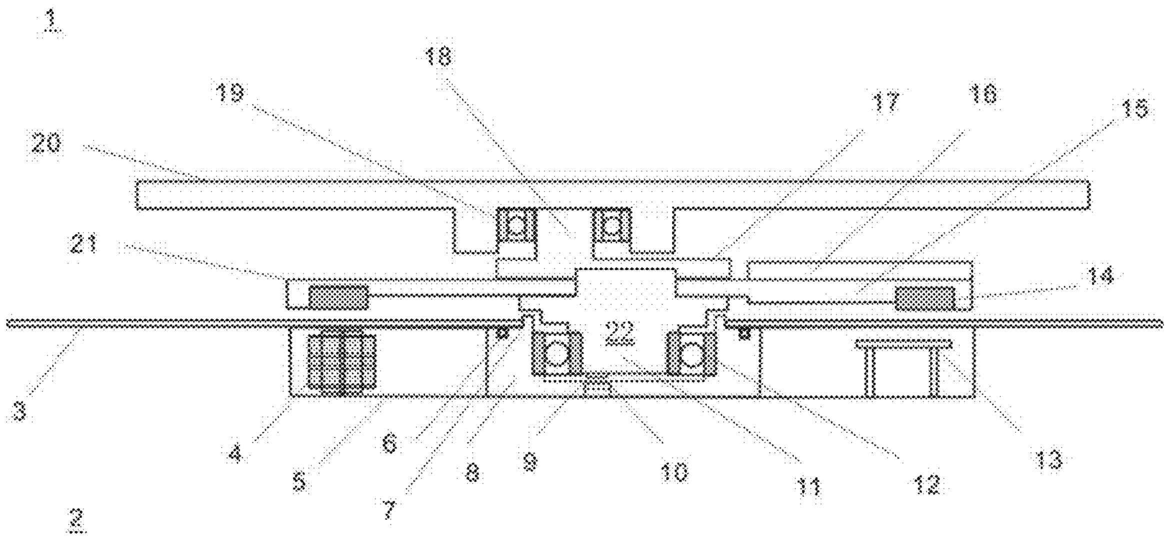
FIG. 1 shows a cross-sectional view of a split shaker according to some embodiments of the present disclosure.

Referring to FIG. 1, it shows a split shaker for an incubator according to some embodiments of the present disclosure. Generally, the incubator may include an incubation chamber 1. In some cases, the incubator may include an incubation chamber and a device chamber 2. One part of the split shaker is for being disposed outside the incubation chamber 1 (e.g., inside the device chamber 2) of the incubator, and another part is for being disposed inside the incubation chamber 1 of the incubator.

The case where the incubator includes an incubation chamber 1 and a device chamber 2 is described below with reference to the drawings. The device chamber 2 and the incubation chamber 1 of the incubator are separated by a base plate 3 of the incubation chamber 1. It should be understood that the incubation chamber 1 and the device chamber 2 of the incubator may be each a sealed space and isolated from each other.

The split shaker described includes a shaking table 20 and a disk drive motor for driving the shaking table 20. Among them, the disk drive motor is also referred to as an axial magnetic field motor, in which an air gap magnetic field is along an axial direction, i.e., a direction of the rotating shaft. For example, CN 110417157 A describes an axial synchronous motor in which a rotating assembly is aligned with the fixed assembly.

The disk drive motor including a stator assembly for being disposed inside the device chamber 2 and a rotor assembly for being disposed inside the incubation chamber 1 and having a central shaft 11 and a rotor turntable 21 mounted on the central shaft 11; wherein the rotation of the rotor turntable 21 drives a shaking movement of the shaking table 20.

Figure 3:
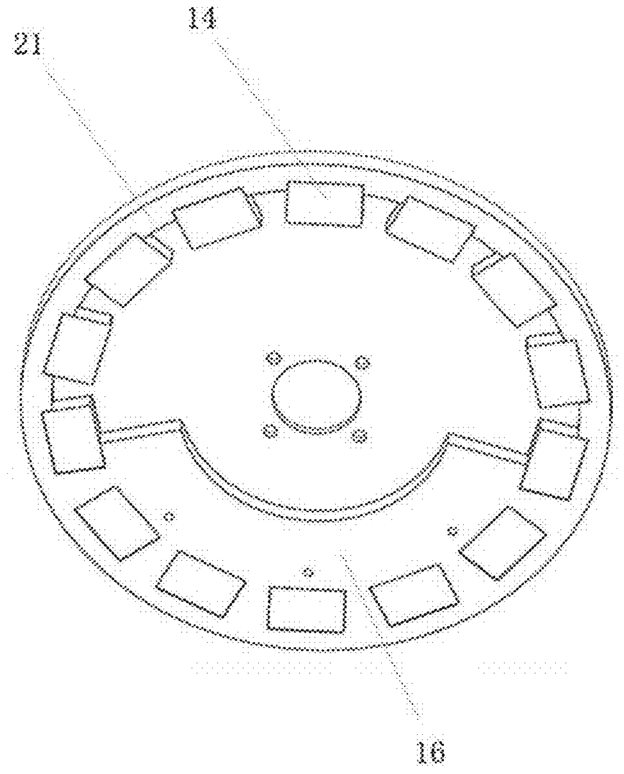
FIG. 3 shows a schematic structural diagram of a rotor turntable according to some embodiments of the present disclosure.

The stator assembly includes a set of electromagnetic coils 4 (i.e., stator coils) arranged annularly. A set of first permanent magnets 14 (i.e., rotor permanent magnets) is disposed in the rotor turntable 21, and the electromagnetic coils 4 are disposed axially opposite to the first permanent magnets 14. For example, the first permanent magnets 14 may be each annularly disposed on a bottom surface of the rotor turntable 21. Alternatively, the bottom surface of the rotor turntable 21 may be provided with a plurality of recesses for accommodating the first permanent magnets 14, as shown in FIG. 3.

Each component of the rotor assembly can be made of stainless steel, and thus can be conveniently disassembled, cleaned and sterilized.

It should be understood that the electromagnetic coils 4 may not be distributed along the entire circumference, but may be distributed over only a portion of the circumference, thereby providing a location for mounting a speed sensor 13 (e.g., a HALL signal sensor) that can detect the speed of rotation of the rotor turntable 21. The speed sensor 13 can detect the rotation of the first permanent magnets 14 during rotation of the rotor assembly.

The stator assembly may further include a stator casing 5. The stator casing 5 is defined internally with sufficient space to mount a heat radiation fan or water cooling pipelines to further cool the electromagnetic coils 4. The stator assembly is wholly disposed within the device chamber 2, so that the possibility that an electric element is introduced into the incubation chamber 1 by the shaker is avoided, which is of great significance for incubation chamber 1 that requires strictly clean incubation environments. And due to the stator assembly being disposed outside the incubation chamber 1, only a small portion of the heat generated by the electromagnetic coils 4 can enter the incubation chamber 1, which is beneficial to ensuring temperature stability inside the incubation chamber 1.

The split shaker may further include a base 8 for fixing to the base plate 3 of the incubation chamber 1 and being located inside the device chamber 2. The base 8 defines an accommodating space 22, and the accommodating space 22 is communicated with the incubation chamber 1. The central shaft 11 of the rotor assembly may be rotatably mounted in the accommodating space 22, e.g. by means of a first bearing 12. The electromagnetic coils 4 of the stator assembly is disposed around the base 8.

The accommodating space 22 may be implemented as a recess to reduce the overall height of the shaker within the incubation chamber 1. Alternatively, the base 8 is provided with a blocking boss 7 at the edge of the accommodating space, and the blocking boss 7 extends to a certain height towards the incubation chamber 1 to prevent the liquid present in the incubation chamber 1 from overflowing into the accommodating space 22. Alternatively, the base 8 is provided with an O-ring 6 and a groove for mounting the O-ring 6 below the base plate 3 of the incubator to achieve sealing of the stator assembly and rotor assembly of the disk drive motor by static sealing. This sealing prevents foreign substances within the incubation chamber 1 from entering into the complex electrical structure of the stator assembly, avoiding the incubation materials from contamination, and facilitating cleaning of the interior of incubation chamber 1 as well.

In some embodiments according to the present disclosure, the split shaker may further include a single-chip microcomputer with a microprocessor (not shown). The electromagnetic coils 4 may be powered by the single-chip microcomputer to generate a periodically varying magnetic field to drive the rotor turntable 21 to rotate.

In some embodiments according to the present disclosure, the central shaft 11 is eccentrically provided with a permanent magnet 9 at the bottom, and a position sensor 10 (e.g., a HALL sensor) is provided in the base 8 to monitor the rotational angular position of the central shaft 11. During rotation of the central shaft 11, the position sensor 10 can detect the position of the permanent magnet 9 and generate a position signal. The single-chip microcomputer can receive the position signal, control the angular position of the central shaft 11 when the rotation is stopped based on the position signal, lock the angular position of the central shaft 11, facilitate the precise control of the shaking, and ensure the safety of cleaning at the optimal stop position. Locking the angular position of the central shaft 11 can be achieved, for example, by applying a certain reverse current to the disk drive motor so that the rotor assembly cannot be rotated manually.

The electromagnetic coils 4, the speed sensor 13 and the position sensor 10 in the stator assembly can be connected to the single-chip microcomputer through cables. Signals are processed by the microprocessor, thus a closed-loop feedback control of the motor speed is achieved, and the stop position of the disk drive motor can be accurately controlled.

The rotor turntable 21 may also be provided with a counterbalance 15 for balancing the centrifugal forces due to the load on the shaking table 20. Optionally the counterbalance 15 and the rotor turntable 12 may be integrally formed. In FIG. 3, for example, the counterbalance 15 is implemented as a thickened part of the rotor turntable 21 and is substantially fan-shaped. Alternatively, the rotor turntable 21 further includes an external counterbalance 16 disposed thereon for further balancing the centrifugal forces due to the load on the shaking table 20. By providing the counterbalance 15 on the rotor turntable, the weight of the external counterbalance 16 can be reduced. The external counterbalance 16 may be implemented as a removable module, thereby allowing for adjustment of the amplitude of vibration, and size and position of the counterbalance.

Figure 2:
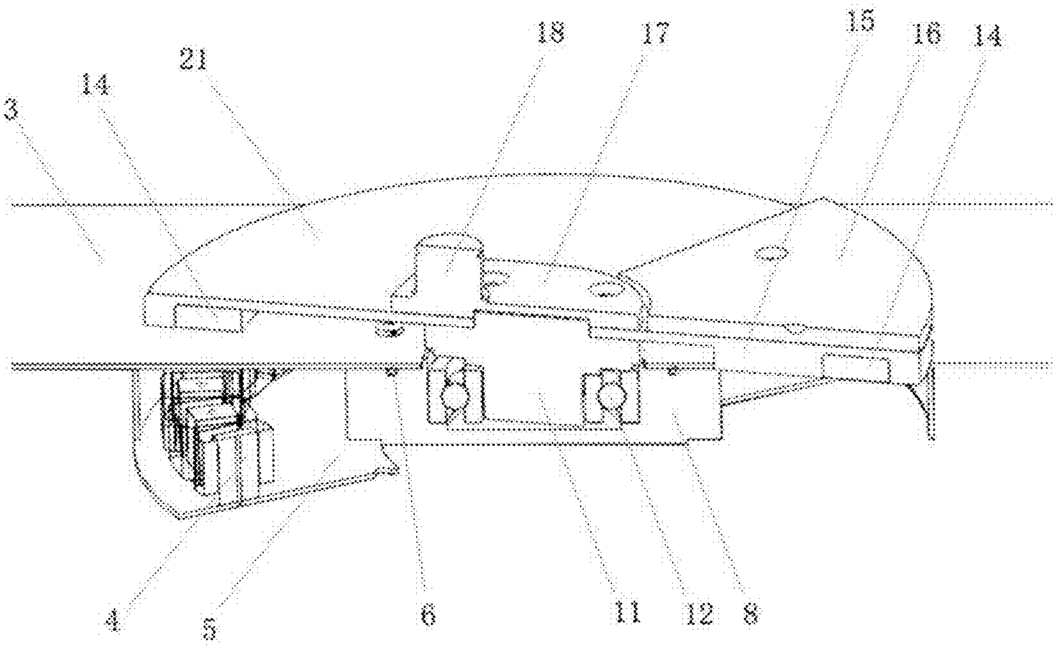
FIG. 2 shows a schematic perspective view of the split shaker of FIG. 1.

An eccentric structure 17 with an eccentric output shaft 18 is connected to the rotor turntable 21. For example, as shown in FIGS. 2 and 3, the central shaft 11 is provided with screw holes on its upper surface, and the rotor turntable 21 is provided with mounting holes, which may be through holes, through which screws pass through the eccentric structure 17 and the rotor turntable 21 to mount them on the central shaft 11. Alternatively, the rotor turntable 21 may be provided with a central opening, with a recess in the bottom surface of the eccentric structure 17. The central shaft 11 extends through the central opening of the rotor turntable 21 and is received in the recess of the eccentric structure 17.

The eccentric structure 17 can be removed, and the amplitude of the shaker can be simply adjusted by replacing structures with different eccentricities. The external counterbalance 16 may also be removed individually and replaced with differently sized and shaped counterbalances to accommodate variations in amplitude, speed range, and load requirements. The eccentric structure 17 and the external counterbalance 16 may also be designed to be adjustable in position within a certain range without disassembly. For example, in general, the amplitude of the shaker may be in the range of 20 to 50 mm, the rotation speed of the shaker may be in the range of 30 to 400 rpm, and the mass of the shaking load may be in the range of 0 to 25 kg.

The shaking table 20 is rotatably mounted on the eccentric structure 17 of the rotor assembly, for example on the eccentric output shaft 18 of the eccentric structure 17 by means of a second bearing 19. The shaking table 20 can be controlled by two pairs of spring strips (not shown) to provide a stop and regulate the shaking modes, such as circular shaking, and reciprocating shaking in either a left-right or front-back direction.

To ensure that all surfaces within the incubation chamber 1 are resistant to chemical attack and easy to clean, the rotor turntable 21, the external counterbalance 16 and the inner walls of the incubation chamber 1 may all be made of stainless steel.

The split shaker according to the present disclosure utilizes the characteristic that there is a certain distance between the stator coils 4 and the rotor permanent magnets 14 of the disk drive motor, allows the base plate 3 of the incubation chamber 1 to be used as a separation plane to separate the stator assembly and the rotor assembly of the disk drive motor, and provides support for the rotor assembly of the disk drive motor by means of the base 8 which can be stably mounted on the base plate 3 or the incubator housing. By means of this split-type structuring manner, the sealed incubation chamber 1 has no heat-generating electromagnetic coils 4, which is advantageous for temperature control in the incubation chamber 1. The incubation chamber 1 has no complex electrical components, which is of great significance for the incubator strictly requiring clean incubation environments. The height of the disk drive motor is low and the stator assembly, which occupies a large portion of the height, is placed in the device chamber 2, so that the height of the shaker in the incubation chamber 1 is relatively low, saving valuable internal space for the incubation chamber 1, and strong vibrations can be avoided at the same time. For example, in one embodiment, the height from the base plate 3 of the incubation chamber to the top of the eccentric output shaft 18 may be only 34 mm.

According to some embodiments of the present disclosure, there is provided an incubator comprising an incubation chamber 1 and, optionally a device chamber 2, and comprising a split shaker according to any of the above split shakers, wherein the stator assembly of the split shaker is disposed outside the incubation chamber 1 and the rotor assembly is disposed inside the incubation chamber 1. In case the incubator comprises an incubation chamber 1 and a device chamber 2, the stator assembly of the split shaker can be disposed in the device chamber 1.

While considerable emphasis has been placed on the preferred embodiments of the invention illustrated and described herein, it will be appreciated that other embodiments, and equivalences thereof, can be made and that many changes can be made in the preferred embodiments without departing from the principles of the invention. Furthermore, the embodiments described above can be combined to form yet other embodiments of the invention of this application. Accordingly, it is to be distinctly understood that the foregoing descriptive matter is to be interpreted merely as illustrative of the invention and not as a limitation.

What is claimed is:

1. An incubator defining an incubation chamber, and comprising a split shaker, wherein the split shaker comprises:

a shaking table;

a disk drive motor for driving the shaking table, comprising a stator assembly disposed outside the incubation chamber, and a rotor assembly disposed inside the incubation chamber and having a central shaft and a rotor turntable mounted on the central shaft; and a base for fixing to a base plate of the incubation chamber and being disposed outside the incubation chamber, the base defining an accommodation space for communicating with the incubation chamber, wherein an edge of the base in the accommodating space is provided with a blocking boss, and the blocking boss extends to a certain height towards the incubation chamber;

wherein the central shaft is rotatably mounted in the accommodating space and in communication with the incubation chamber;

wherein rotation of the rotor turntable drives a shaking movement of the shaking table.

2. The incubator of claim 1, wherein the stator assembly comprises electromagnetic coils and first permanent magnets disposed in the rotor turntable, and wherein the electromagnetic coils are axially opposite to the first permanent magnets.

3. The incubator of claim 1, wherein:

the split shaker further comprises an eccentric structure mounted on the rotor turntable, and comprising an eccentric output shaft;

the shaking table is rotatably mounted on the eccentric output shaft, and the rotation of the eccentric structure drives an shaking movement of the shaking table.

4. The incubator of claim 1, wherein the rotor turntable is provided with a counterbalance.

5. The incubator of claim 4, wherein the rotor turntable is further provided with an externa counterbalance.

6. The incubator of claim 1, wherein the accommodating space is sealed from a space outside the incubation chamber by an O-ring and a groove for mounting the O-ring, wherein the O-ring and the groove are disposed on the base, below the base plate of the incubation chamber, so that the accommodating space is sealed from the space outside the incubation chamber.

7. The incubator of claim 1, wherein a second permanent magnet is eccentrically disposed at a bottom portion of the central shaft, and a HALL sensor is embedded in the base to monitor a rotational angular position of the central shaft.

* * * * *